United States Patent [19]

Hahnenberger

[11] Patent Number: 5,908,866

[45] Date of Patent: Jun. 1, 1999

[54] PHARMACEUTICAL COMPOSITION CONTAINING CARBACHOL AND OTHER CHOLINERGIC SUBSTANCES

[75] Inventor: Rudolph Wolfgang Hahnenberger, Uppsala, Sweden

[73] Assignee: Astra Aktiebolag, Sodertalje, Sweden

[21] Appl. No.: 08/908,375

[22] Filed: Aug. 7, 1997

Related U.S. Application Data

[63] Continuation of application No. 08/326,797, Oct. 20, 1994, Pat. No. 5,679,713, which is a continuation of application No. 07/927,831, Aug. 10, 1992, abandoned.

[51] Int. Cl.[6] .................................................. A61K 31/14

[52] U.S. Cl. ............................................ 514/642; 514/912

[58] Field of Search .................................... 514/642, 912

[56] References Cited

U.S. PATENT DOCUMENTS

| 2,185,220 | 1/1940 | Nabenhauer | 167/65 |
| 4,804,539 | 2/1989 | Guo et al. | 424/450 |

*Primary Examiner*—Zohreh Fay
*Attorney, Agent, or Firm*—White & Case L.L.P.

[57] ABSTRACT

The present invention relates to the use carbachol and other cholinergic substances for the treatment of keratoconjunctivitis sicca.

9 Claims, No Drawings

PHARMACEUTICAL COMPOSITION CONTAINING CARBACHOL AND OTHER CHOLINERGIC SUBSTANCES

This application is a continuation of application Ser. No. 08/326,797, filed on Oct. 20, 1994, now U.S. Pat. No. 5,679,713 which is a continuation of application Ser. No. 07/927,831, filed Aug. 10, 1992, now abandoned.

FIELD OF THE INVENTION

The present invention relates to the use of carbacholin as an active agent in pharmaceutical compositions for the treatment of keratoconjunctivitis sicca (dry eyes). The invention specifically concerns such use in eyedrops having the ability to stimulate natural tear production.

BACKGROUND ART

Dry eyes (keratoconjunctivitis sicca, KCS) is a disease characterised in reduced secretion of tears. Cornea and conjunctiva suffer from an inferior function of tear supply resulting in structural changes as epithelial cell death, corneal infiltrations and others. Patients are afflicted with smarting pain, sensations of dust, occasionally reduced vision, aches, irritation and so on. In its classical form KCS appears as Sjögren's syndrom involving engagement of other serous glands but KCS is much more common in its less serious form. It has been estimated that about 25% of the patients in an eye clinic suffer from more or less chronically dry eyes (Scharf, J., Zonis, S., Perelman J. and Hit, E., Harefuah., 1975, 89, p 505).

Treatment of dry eyes is today a major problem in ophtalmology. So far tear substitutions have mostly been offered to patients. Tear substitutions normally consist of salt solutions with a lubricant e.g. methyl cellulose, polyvinyl alcohol and hyaluronic acid. One important disadvantage of this treatment is its very short time of action (Duke Elder, Systems of Ophtalmology Volume XIII Part II p 634, 1974). Another disadvantage of most tear substitutes is that they contain benzalkonium, which has a damaging impact on eyes of mammals (Pjister, R. R. and Burstein, N., Invest Ophtalmol. 15:246, 1976). Also, many pharmaceutical formulations are very poorly adapted to the natural specific composition or electrolytic status of natural tear fluid (Gilbard, J. P., Rossi, S. R. and Heyda, K. G., American J of ophtalmology 10 107:348–355, 1989).

Carbachol chloride is a well-known substance in the treatment of glaucoma. For this indication its ability of lowering intraocular pressure is employed. Here, carbachol chloride is normally used in a concentration of 3% and in combination with benzalconium chloride in order to obtain good penetration of the eye (Smolen, V. F., Clevenger, J. M., Williams, E. J. and Bergdolt, M. W., J of Pharmaceutical Sciences, 1973, 62 p 958). Other than having this effect, benzalconium chloride in pharmaceutical mixtures has a preservative function. Other effects of carbachol chloride exposure to the eye are tear secretion, miosis and influence on the accomodatory ability of the eye. These so called cholinergic effects are in this context considered as side effects.

Substances having the same effects as carbachol chloride are methacholine chloride, methanecholine bromide, bethanechol chloride, furtrethonium iodide and arecholine.

Tear production can be stimulated also by other cholinergic substances such as acetylcholine, pilocarpine, physostigmine, neostigmine and others. These compounds, however, easily penetrate the cornea upon exposure, thereby activating cholinergically innervated intraocular structures such as the pupillary sphincter and the accomodation muscle, both unwanted side effects in cases where only extraocular effects are wanted. Such compounds, therefore, are less suited for this purpose than is carbachol.

DISCLOSURE OF THE INVENTION

The present invention concerns a novel pharmaceutical preparation containing cholinergic substances based on carbachol, methacholine, bethanechol, furtrethonum or arecholine, especially carbachol chloride, methanecholine chloride, methanecholine bromide, bethanechol chloride, furtrethonium iodide and arecholine as active agent for the treatment of KCS and the use of carbachol for treatment of this disease. These substances actively stimulate the secretion of tears in mammals including man, resulting in a longer duration of the effect than is usually the case with medicaments not containing this type of component. For carbachol chloride the frequency of application can be kept as low as 3–4 times per day as compared to twice per hour with no carbachol present.

Carbachol chloride, methanecholine chloride, methanecholine bromide, bethanechol chloride, furtrethonium iodide and arecholine without addition of benzalkonium chloride have very little effect on the intraocular pressure but stimulate glands outside the eye to increased tear secretion. In low doses i.e. low concentrations no other effect than tear secretion can be observed. The present invention makes use of this property of these substances in that low concentrations are used for the purpose. For the treatment of KCS in mammals, including man, an effective amount ranging from 5 μg to 600 μg of any of the above-mentioned cholinergic compounds is administered to a host in need of such treatment.

Patients treated with eye drops containing carbachol according to the invention have experienced a strong relief in their symptoms in that their eyes feel less irritated than after using other preparations. Also, the effect of treatment is longer. Of 52 treated patients only 6 have had no effect or side effects of the treatment.

Methods of preparation

Solutions for application in the eye must, according to hygienic requirements be sterile. Sterility is also required in order to protect solutions containing carbachol from decomposing. Preservatives must not be added since they can cause damage to the eye. Concentrations of carbachol should preferably be between 0.01–1 percent by weight. The solution should be made isotonic or hypotonic. Additives of polymeric substances such as hypromellose, metyl cellulose, polyvinyl alcohol or hyaluronic acid could prolong the effect of carbachol.

Methods of pharmaceutical preparation

Solutions for use as eyedrops are preferentially prepared by first aseptically mixing of all the necessary ingredients i.e. the active substance, salts and lubricant. If necessary the pH is adjusted to 5–7 using solutions of NaOH, KOH, HCl or boric acid. The solution is then sterilised by autoclaving or sterile filtration and filled on one dose packings.

Solutions could also be prepared by first preparing solutions of each of the ingredients and then sterilising these solutions in the same manner as above before finally mixing and filling the solutions on one dose packings under aseptical conditions.

Examples of pharmaceutical formulations

| | | |
|---|---|---|
| Carbachol chloride | 0.01–1.0 | g |
| Sodium choloride | 0.5–0.09 | g |
| Water for injection | ad 100 | g |
| Carbachol chloride | 0.01–1.0 | g |
| Boric acid | 1.15–3.0 | g |
| Water for injection | ad 100 | g |
| Carbachol chloride | 0.01–1.0 | g |
| Polyvinyl alcohol | 1.4 | g |
| Sodium chloride | 0.5–0.9 | g |
| Water for injection | ad 100 | g |
| Carbachol chloride | 0.01–1.0 | g |
| Methyl cellulose | 0.5–1.0 | g |
| Sodium chloride | 0.5–0.9 | g |
| Water for injection | ad 100 | g |
| Carbachol chloride | 0.01–1.0 | g |
| Polyvinyl alcohol | 1.4 | g |
| Sodium chloride | 0.45 | g |
| Potassium chloride | 0.37 | g |
| Water for injection | ad 100 | g |

The eyedrops according to the formulations suggested can be applied directly to the eye either upon need or 3–4 times daily.

I claim:

1. A sterile pharmaceutical solution without an added preservative for topical ocular treatment of Dry Eyes disease or keratoconjunctivitis sicca (KCS) comprising: an active ingredient at a therapeutic dosage ranging from 5 µg to 600 µg and at a low concentration of 0.01 to 1 percent by weight, selected from the group consisting of carbachol, methacholine, bethanechol, furtrethonium and arecoline; and a pharmaceutically acceptable isotonic or hypotonic salt solution at a pH range of 5 to 7.

2. A sterile pharmaceutical composition without added preservatives for topical ocular treatment of dry eyes disease or keratoconjunctivitis sicca (KCS) comprising an active ingredient at a therapeutic dosage ranging from 5 µg to 600 µg in a concentration of 0.01 to 1 percent by weight selected from the group consisting of carbachol, methacholine, bethanechol, furtrethonium and arecoline, and a pharmaceutically acceptable carrier.

3. The pharmaceutical composition of claim 2 wherein the active ingredient is a compound selected from the group consisting of carbachol chloride, methanecholine chloride, methanecholine bromide, bethanechol chloride, furtrethonium iodide and arecoline.

4. The pharmaceutical composition of claim 2 or 3 wherein the pharmaceutically acceptable carrier is an isotonic or hypotonic salt solution.

5. The pharmaceutical composition of claim 4, which further comprises a pharmaceutically acceptable polymer.

6. The pharmaceutical composition of claim 5 wherein the polymer is selected from the group consisting of hypromellose, methyl cellulose, polyvinyl alcohol, and hyaluronic acid.

7. The pharmaceutical composition of claim 5 wherein the active ingredient is carbachol chloride.

8. The pharmaceutical composition of claim 4 wherein the solution has a pH range from 5–7.

9. Eye drops for the topical ocular treatment of dry eyes disease or keratconjunctivitis sicca (KCS) comprising the sterile pharmaceutical composition of any of claims 2–8.

* * * * *